US005709702A

United States Patent [19]
Cogita

[11] Patent Number: 5,709,702
[45] Date of Patent: Jan. 20, 1998

[54] SURGICAL DEVICE FOR REPAIRING ANEURYSMS

[76] Inventor: Giuseppe Cogita, 11506 Newport Mill Rd., Silver Spring, Md. 20902

[21] Appl. No.: 730,456

[22] Filed: Oct. 15, 1996

[51] Int. Cl.⁶ .......................... A61M 29/00; A61B 17/00
[52] U.S. Cl. ............................................. 606/198; 623/1
[58] Field of Search ........................... 606/1, 108, 191, 606/192, 194, 195, 198; 604/96; 128/898, 899; 623/1, 12

[56] References Cited

U.S. PATENT DOCUMENTS

| | | | |
|---|---|---|---|
| 4,990,055 | 2/1991 | Wilkoff | 606/198 |
| 5,282,823 | 2/1994 | Schwartz et al. | 606/198 |
| 5,344,425 | 9/1994 | Sawyer | 606/198 |
| 5,476,505 | 12/1995 | Limon | 606/198 |
| 5,514,176 | 5/1996 | Bosley, Jr. | 623/1 |

FOREIGN PATENT DOCUMENTS 9214408  9/1992  WIPO .................... 606/198

*Primary Examiner*—William Lewis
*Attorney, Agent, or Firm*—Lane, Aitken & McCann

[57] ABSTRACT

A surgical device is provided to reduce the size of and relieve the pressure within an aneurysm. The surgical device is comprised of catheter tubing containing a spring wound under stress. The catheter is inserted through the aneurysm to be repaired and the catheter is then pulled back leaving the spring to expand within the aneurysm. The spring has a one-way helical flap mounted between the spring coils. The flap allows the blood to flow from the swollen part of the aneurysm but not to enter it.

7 Claims, 5 Drawing Sheets

SURGICAL DEVICE FOR REPAIRING ANEURYSMS

DESCRIPTION OF THE INVENTION

The present invention relates to a surgical device that is used to repair an aneurysm.

BACKGROUND OF THE INVENTION

An aneurysm is a localized dilation of a blood vessel, usually an artery, due to a weakening of the vessel wall. The dialyzed portion of the vessel wall expands and contracts with the rise and fall of the blood pressure within the vessel. If left untreated, the aneurysm will continue to expand and will eventually rupture, usually resulting in a fatal hemorrhage.

Aneurysms are usually treated by relatively high risk surgery involving prosthetic graft replacement of the diseased artery. Aneurysms can also be treated by placing a flexible woven tube within the aneurysm. Alternatively, they are treated with drugs.

OBJECTS OF THE INVENTION

It is an object of the invention to stop systolic pulsing in an aneurysm and to lower blood pressure in the aneurysm during the diastolic phase of the heat beat.

A further object of the invention is to insert a spring loaded one-way valve against the inner wall of an artery at the site of leakage of arterial blood into an aneurysm.

SUMMARY OF THE INVENTION

The present invention is an improved surgical device which relieves systolic pressure within an aneurysm. It is comprised of catheter tubing having a distal end with pie-shaped flaps, and a stent in the form of a helical coil spring. The spring is compressed to a smaller diameter by winding the coil of the spring tighter, and is inserted into the catheter tubing. One end of the spring is positioned in the distal end of the catheter tubing and the other end of the spring is engaged by a ram within the catheter tubing. The spring is open at both ends and has a one-way valve in the form of a helical flap between the coils of the spring.

The catheter tubing is inserted into the artery on one side of the aneurysm and is pushed through the artery to position the spring within the catheter to bridge the site of blood leakage into the aneurysm. After insertion, the catheter tubing is pulled back while using the ram to hold the spring in place within the artery at the aneurysm. As the spring emerges from the catheter, it expands and causes the pie-shaped flaps to open and expand against the interior of the blood vessel wall. As the spring expands, it unwinds and slides along the ramps formed by the expanded pie-shaped flaps of the receding catheter. When the pressure rises in the artery, the helical flap on the spring within the aneurysm prevents the flow of blood into the swollen part of the aneurysm and prevents the application of systolic pressure to the swollen part of the aneurysm. When the pressure in the vessel falls, high blood pressure in the swollen part of the aneurysm is relieved through the helical flap.

DETAILED DESCRIPTION OF THE PREFERRED EMBODIMENTS

Figure 1:
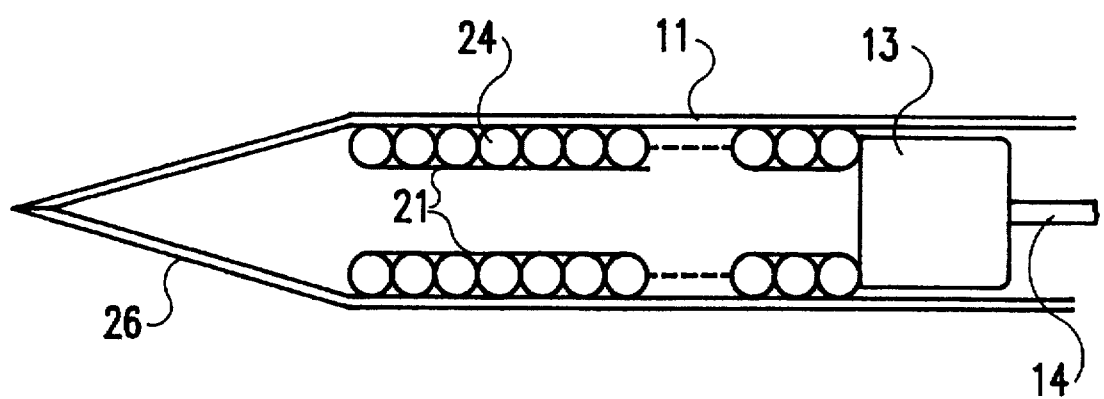
FIG. 1 is an axial sectional view of the surgical device of the present invention.
Figure 3:
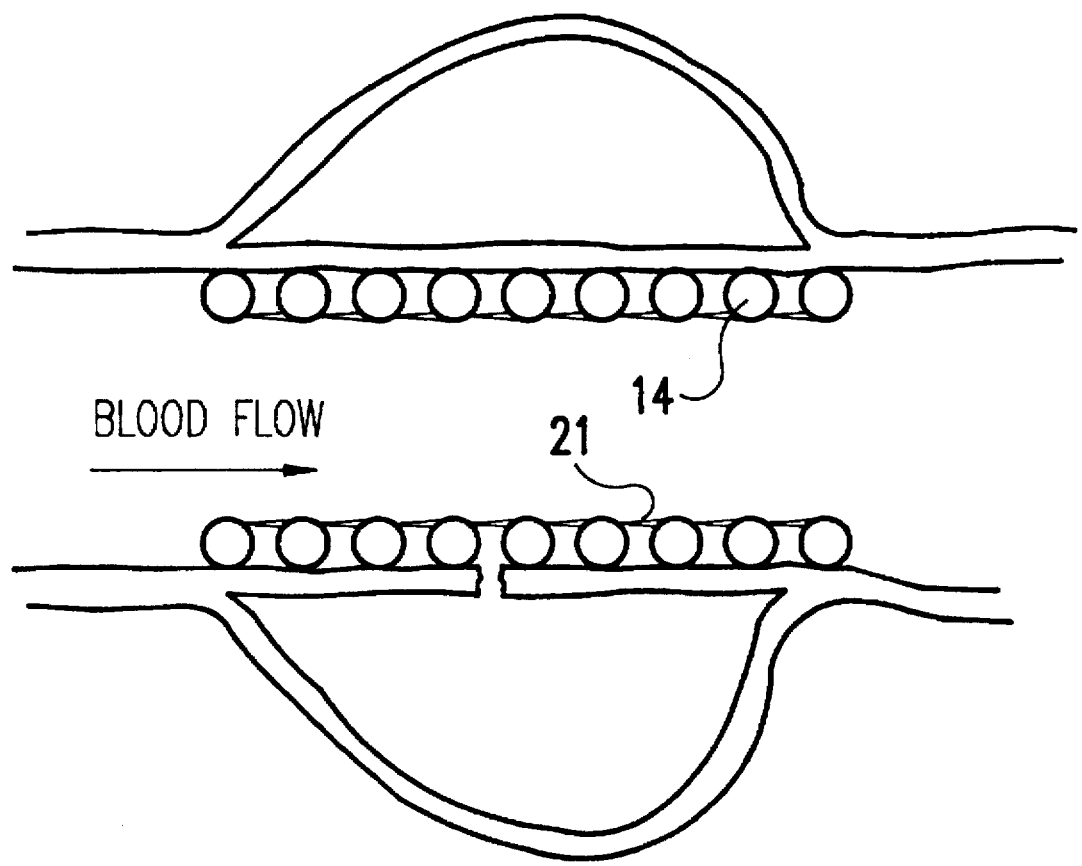
FIG. 3 is an enlarged axial sectional view of a portion of the stent of the invention showing the details of the coil and flap structure of the stent.
Figure 4:
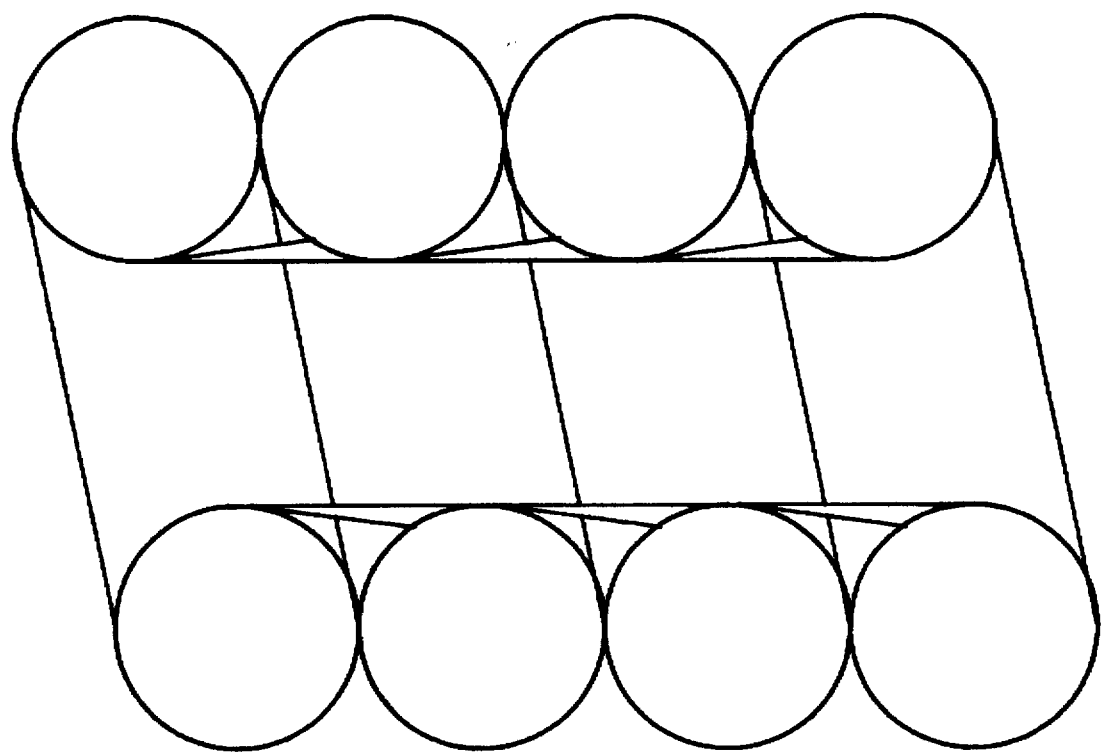
FIG. 4 is an enlarged axial sectional view of the stent of the invention in place within an aneurysm with the catheter tubing completely removed.
Figure 5:
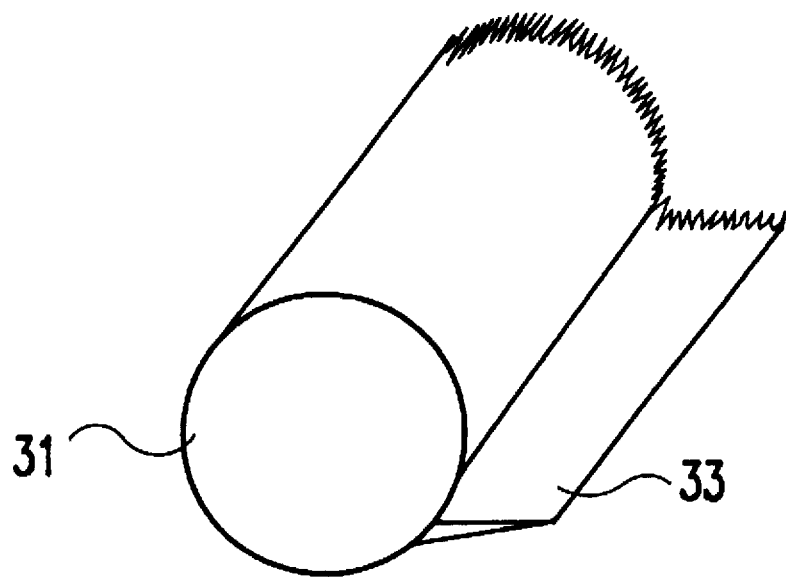
FIG. 5 illustrates a fragmentary view of a linear stock of material which can be formed into the stent of the invention.

As shown in FIG. 1, a stent in the form of a spring 24 is enclosed within a catheter 11. The spring is preferably made out of super elastic material, such as nickel-titanium alloy sold under the names Tinel or Nitinol. The spring is coaxially wound under stress so as to be of a smaller diameter and so that the spring will expand radially when released from the catheter 11. Within the catheter, the coils of the spring 24 have little or no space between them. A helical flap 21 extends between the coils of the spring on the radially inward side of the coils. As best shown in the enlarged view of FIG. 3, the flap 21 may be made out of a flexible elastomeric material and has one side permanently cemented to the spring coil and has the other side biased in engagement with the adjacent loop of the coil so as to form a valve which permits flow through the flap from outside of the spring coils to the inside of the spring coil, but not vice versa. Alternatively, the spring and flap may be a one-piece structure formed from linear stock of the superelastic material. FIG. 5 illustrates a fragmentary view of the linear stock in which a cylindrical rod 31 is formed of one piece with flap 33. When the linear stock is worked into a helical spring shape, the flap 33 will form a one-way valve on the coils of the spring.

A ram 13 as shown in FIG. 1 abuts the proximal end of the spring, but is not attached to the spring. The ram 13 is supported on the end of a stiff flexible wire 14 extending back through the catheter.

Figure 2:
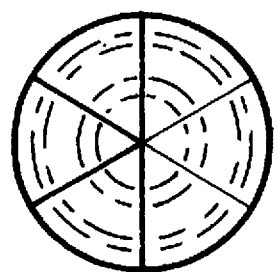
FIG. 2 is an end view of the surgical device of FIG. 1 showing the flaps at the distal end of the surgical device.

To effect the repair of an aneurysm, the catheter tubing 11 is inserted into the artery and pushed past the site of the aneurysm to be repaired so that the spring bridges the site of blood leakage into the aneurysm. The helical flap should project in the opposite direction from blood flow within the artery. Accordingly, if the catheter is inserted through the aneurysm from the downstream side, the flap should extend toward the distal end of the catheter as shown in FIG. 1. The catheter tubing is then pulled back while using the ram to hold the spring 24 in place. As the catheter tubing is pulled back, the wire 14 used to maintain the position of the ram 13, which holds the spring in place in the artery. As shown in FIGS. 1 and 2, the distal end of the catheter is formed into a cone shape comprising flexible pie shaped flaps 26, which are pushed outwardly by the spring as the spring emerges from the catheter. The pie-shaped flaps have a dimension in the axial direction of the catheter so that when they are pushed outwardly, they will engage the inner surface of the blood vessel wall. As the spring 24 expands and unwinds upon emerging from the catheter 11, the coils of the spring separate and slide down the ramp formed by the pie-shaped flaps. The slope of the ramp formed by the open flaps is gradual enough so that the unattached end of the helical flap 21 remains in engagement with the adjacent spring coil loop and the helical flap orientation providing the one-way valve function is not interferred with. When the entire spring has emerged from the catheter, the catheter and the ram are withdrawn from the artery as a unit leaving the spring in place. To insure that the spring has been completely pushed out of the catheter, part of the ram has to project from the catheter. The axial dimension of the ram is made long enough to avoid any danger of the ram coming all the way out of the catheter as the spring is pushed out.

The spring 24 expands against the blood vessel wall upon emerging from the catheter, and the flap 21 forms a one-way flow barrier at the site of blood leakage into the aneurysm. When the pressure in the artery rises to the systolic pressure, the flap 21 is held closed by the pressure in the artery and blood does not flow from the vessel into the swollen part of the aneurysm. When the blood pressure in the vessel decreases to the diastolic pressure, higher pressure in the aneurysm will be relieved by the flow of blood out of the swollen portion of the aneurysm through the helical flap. In this manner, the spring with the helical flap relieves systolic pressure from the swollen part of the aneurysm preventing further enlargement of the aneurysm and greatly reducing the danger of aneurysm rupture.

While the invention has been described in terms of the aforementioned embodiments, those skilled in the art will recognize that the invention can be practiced with modification within the spirit and scope of the appended claims.

I claim:

1. A surgical device, comprising:

a length of flexible catheter tubing; and a helical coil spring within said catheter tubing, said spring being wound under stress within said catheter tubing so that said spring will expand radially when released from said catheter tubing, a helical flap positioned between the coils of said helical spring and attached on one side thereof to said spring, said flap being arranged to allow flow from the exterior of said spring to the interior of the spring, but prevent flow through the coils of said spring from the interior of said spring to the exterior of the spring.

2. A surgical device according to claim 1, wherein said spring is coaxially wound so that there is substantially no space between the coils of said spring within said catheter tubing, said coils separating when said spring expands upon release from said catheter tubing.

3. A surgical device as recited in claim 1, further comprising a ram within said catheter tubing engaging the distal end of said spring to hold said spring in place within an artery while said catheter tubing is pulled back to release said spring in an artery.

4. A method of repairing an aneurysm, using the surgical device of claim 1, comprising the steps of:

placing said surgical device in an artery at the site of said aneurysm; and pulling said catheter tubing back leaving said spring in said artery and removing said tubing from said blood vessel, thereby releasing said spring so that so spring expands at the site of said aneurysm, said spring relieving the swollen part of said aneurysm of systolic pressure by permitting flow from the swollen part of said aneurysm through the coils of said spring but preventing flow from within said spring through the coils of said spring into the swollen part of said aneurysm.

5. A method as recited in claim 4, wherein said spring is held in place within a blood vessel at the site of an aneurysm as said catheter tubing is pulled back by means of a ram within said catheter tubing engaging a distal end of said spring within said catheter.

6. A surgical device, comprising:

a length of flexible catheter tubing; and a helical coil spring within said catheter tubing, said spring being wound under stress within said catheter tubing so that said spring will expand radially when released from said catheter tubing, said catheter tubing being tapered at said distal end, and said distal end being further comprised of pie-shaped flexible flaps.

7. A stent for repairing an aneurysm comprising a helical coil spring, a helical one-way flap positioned between the coils of said spring and attached on one side thereof to said spring, said flap being arranged to permit radially inward flow through the coils of said spring and to prevent radially outward flow through the coils of said spring.

* * * * *